United States Patent [19]

Gavras

[11] Patent Number: 4,762,820

[45] Date of Patent: Aug. 9, 1988

[54] THERAPEUTIC TREATMENT FOR CONGESTIVE HEART FAILURE

[75] Inventor: Haralambos Gavras, Wayland, Mass.

[73] Assignee: Trustees of Boston University, Boston, Mass.

[21] Appl. No.: 835,487

[22] Filed: Mar. 3, 1986

[51] Int. Cl.⁴ .............................................. A61K 37/02
[52] U.S. Cl. ........................................ 514/10; 514/11; 514/805
[58] Field of Search ............................ 514/10, 11, 807

[56] References Cited

FOREIGN PATENT DOCUMENTS 0061356 9/1982 European Pat. Off. .

OTHER PUBLICATIONS

Cecil Textbook of Medicines, Ed. Wyngaarden, W. B. Saunders Co., Philadelphia, 1982, p. 1025.

Nicod et al., *The American Journal of Cardialogy*, 55, 1043–1047 (1985).

Primary Examiner—J. R. Brown
Assistant Examiner—F. T. Moezie
Attorney, Agent, or Firm—David Prashker

[57] ABSTRACT

A novel therapeutic method for treating human and animal subjects afflicted with congestive heart failure is provided by administering effective dosages of a selective antagonist for arginine vasopressin to the subject. The antagonist is an effective and potent inhibitor for vasopressin and is a therapeutic agent selected from the class consisting of analogues of previously prepared compositions synthesized in a conventionally known manner. The administration of such selective antagonist as a therapeutic agent results in a demonstrated beneficial change in approximately thirty percent of tested individuals.

5 Claims, 1 Drawing Sheet

THERAPEUTIC TREATMENT FOR CONGESTIVE HEART FAILURE

FIELD OF THE INVENTION

The invention is concerned generally with therapeutic regimens for specific pathological states in human subjects and is particularly directed to therapeutic agents for treatment of congestive heart failure in human patients.

BACKGROUND OF THE INVENTION

Congestive heart failure is a diseased state in which there is circulatory congestion, and abnormal accumulation of fluid in the organs and blood of a subject, which is secondary to heart failure. The diseased condition occurs when the volume of blood delivered into the systemic circulation is chronically reduced and when one or both ventricles of the heart fail to expel the normal fraction of the blood delivered to it. In these instances, a complex sequence of biochemical and anatomical adjustments occurs that ultimately results in an abnormal accumulation of fluid in the heart and blood vessels. Initially, there may be heart failure without congestion, but if the process continues in normal development, congestive heart failure will ensue rapidly or gradually. The hallmark of congestive heart failure is a decreased cardiac output associated with an abnormally elevated peripheral vascular resistance.

Although the term "congestive heart failure" usually denotes failure of both ventricles, most typically it is an initial dysfunction of the left side that results in the subsequent failure of the right side. The accompanying venous congestion usually involves both the pulmonary and systemic capillary beds, but congestion may be limited to either one alone.

Individuals suffering from this condition frequently exhibit breathlessness which worsens with increasing physical activity (which demands an increased cardiac output). This symptom results from elevated pulmonary venous and capillary pressures that force fluid into the interstitium of the lung thereby increasing the work of breathing. Often the fluid transudes into the alveolar spaces of the lung causing pulmonary oedema; night time episodes of pulmonary oedema are common symptoms of pulmonary venous congestion. Right-sided heart failure elevates systemic venous pressure; its principal symptoms are peripheral oedema and abdominal discomfort from hepatic enlargement.

Physical examination of afflicted persons demonstrates a variety of additional signs and symptoms. Often, a lowered cardiac output causes the person to appear pale and clammy. The presence of alveolar fluid may be detected as rales on lung examination. Systemic venous hypertension is demonstrated by elevated jugular venous pressure, liver engorgement and peripheral oedema. Frequently the heart is also enlarged. A third heart sound may often be heard which is an indication of reduced left ventricular compliance; a fourth heart sound may also be present. A chest radiograph usually confirms the existence of cardiac enlargement and shows venous redistribution or overt pulmonary oedema.

The treatment of congestive heart failure is aimed at correcting the basic physiological derangements. Oxygen may be given to improve pulmonary gas exchange; diuretics may be given to reduce venous hypertension and cardiac filling; often, a drug which improves myocardial contractility is given. Recently, drugs that reduce the elevated systemic vascular resistance or "afterload" have become increasingly popular, both for acute and chronic treatment of this condition. When the acute symptoms have been abated, a search for the etiology of heart failure is then undertaken. Although the prognosis depends on the underlying cause, less than fifty percent of those individuals afflicted with congestive heart failure are alive five years after onset of the clinical condition.

One of the primary difficulties in treating human patients with congestive heart failure is that the causes or sources of the elevated systemic vascular resistance and oedema are varied and are mostly due to changes and adjustments in three different vasopressor systems of the body, each of which interacts directly with the others. These are: the sympathetic nervous system stimulations; the renin-angiotensin system; and neurohypophyseal secretion of vasopressin (antidiuretic hormone or arginine vasopressin).

The sympathetic nervous system is a part of the autonomic nervous system and represents a series of peripheral spinal nerves which innervate most visceral organs, the sweat glands and blood vessels of the body, and the skeletal muscles. Stimulation of particular sympathic nerves effects dilation of the pupils; vasoconstriction of the blood vessels of the skin and viscera; vasodilation of the blood vessels of skeletal muscles, cardiac muscle and the skin of the face; and contraction of the splenic capsule which directly results in the expulsion of red blood cells into the systemic circulation. Such stimulation also increases sweat secretion, increases the heart rate, and increases the release of renin from the kidney.

The activity of the renin-angiotension system biochemically involves a class of polypeptide hormones derived from an angiotensinogen precursor substrate by action of the proteolytic enzyme renin, which is itself secreted by the juxtaglomerular cells in the kidney. The enzyme renin is secreted in response to low blood volume, a decreased of blood pressure, or an increased stimulation of the renal sympathetic nerves. This enzyme acts upon angiotensinogen to release the polypeptide angiotensin I, which in turn is converted into angiotensin II. Angiotensin II which is an octapeptide hormone and one of the most powerful vasoconstrictor known. Its main actions are constriction of arterioles to increase blood pressure and stimulation of the adrenal zona glomerulosa to secrete aldosterone, a hormone that acts on the kidney to cause retention of salt and fluid. Angiotensin II also performs a variety of other roles including: exerting a negative feedback effect on the juxtaglomerular cells to decrease the rate of renin secretion; acting upon receptor areas in the brain that in turn stimulate an increase in water uptake and vasopressin secretion; and modulating sympathetic nerve functions via its action upon peripheral neurons.

Vasopressin, also known as antidiuretic hormone and arginine vasopressin, is a cyclic polypeptide that is formed in the hypothalamus and is stored in the posterior lobe of the pituitary gland. Vasopressin is released into the body as necessary to stimulate smooth muscle in the walls of small blood vessels to contract and to raise the overall blood pressure of the body. Vasopressin also conserves body water by promoting reabsorption of water in the distal convoluted tubules of the kidney thus resulting in more concentrated urine.

In persons afflicted with congestive heart failure, the elevated vascular resistance has been empirically demonstrated to result partly from sympathetic nervous system stimulation and partly from increased activity of the renin-angiotensin system [Zelis and Flaim, *Prog. Cardiovasc. Dis.* 24: 437–459 (1982)]. Some investigators have also speculated that the secretion of vasopressin may also be directly involved in the pathological state since its concentration is often, but not always, increased in those patients afflicted with congestive heart failure [Yamane, Y., *Jpn. Circ. J.* 32: 745-759 (1968); Riegger et al., *Am. J. Med.* 72: 49-52 (1982); Szatalowicz et al., *N. Engl. J. Med.* 305: 263-266 (1981); Goldsmith et al., *J. Am. Coll. Cardiol.* 1: 1385-1390 (1983); Preibisz et al. *Hypertension* 5: 1129-1138 (1983)]. Similarly, elevated plasma levels of vasopressin have been reported in animal studies with subjects demonstrating low output heart failure [Anderson et al., *J. Clin. Invest.* 54: 1473-1479 (1974); Riegger and Liebau, *Clin. Sci.* 62: 465-469 (1982); Thrasher et al., *Am. J. Physiol.* 244: R850-856 (1983)].

Experimentally, it has been demonstrated that vasoconstriction does not occur when physiological doses of arginine-vasopressin (hereinafter "AVP") are applied to the femoral artery [Monos et al., *Am. J. Physiol.* 234: H167-172 (1978)]. Animal studies have shown that AVP, when endogenously oversecreted during dehydration, hemorrhage or hyperosmolality, has a vasopressor effect [Montani et al. *Circ. Res.* 47: 346-355 (1980); Aisenbrey et al., *J. Clin. Invest.* 67: 961-968 (1981)] and that such levels of vasopressin have a more pronounced pressor action in animals subjected to baroreceptor denervation, sympathectomy and/or nephrectomy [Cowley et al., *Circ. Res.* 46: 58-67 (1980); Gavras et al., *Hypertension* 4: 400-405 (1982)]. In addition, the AVP concentration present in patients with congestive heart failure enhances the renal tubular reabsorption of water [Bercu et al., *Circulation* 2: 409-413 (1950); Leaf and Mamby, *J. Clin. Invest.* 31: 60-71 (1952); White et al., *J. Clin. Invest.* 32: 931-939 (1953)].

Relatively few studies have actually examined the vasopressor effect of endogenous AVP in human subjects. Recently, using an antagonist of AVP at the vascular $V_1$ receptors, it was demonstrated that when administered to normally hydrated healthy human subjects, this AVP antagonist did not alter blood pressure [Manning et al., *J. Med. Chem.* 25: 45-50 (1982); Bussin et al., *Am. J. Physiol.* 246: H143-147 (1984)]; subsequent investigations revealed, however, that this AVP antagonist did in fact decrease the blood pressure in sodium-loaded patients with end-stage renal disease in whom plasma AVP concentration was found to be increased above normal values [Gavras et al., *Hypertension* (Suppl. I) 6: 156-160 (1984)].

It is readily recognized, therefore, that the relationship of vasopressin to the renin-angiotensin system and the sympathetic nervous system is a complex and poorly understood phenomenon. Angiotension II has been reported to usually increase vasopressin levels; similarly, there have been reports that norepinephrine decreases the effectiveness of vasopressin. Insofar as is presently known, however, there is no information whether concentrations of vasopressin above normal levels are able to cause vasoconstriction in human patients with congestive heart failure. Furthermore, there is no knowledge and no factual basis upon which to predict whether a selective antagonist could act as a therapeutic agent to provide a decrease in systemic vascular resistance in persons afflicted with congestive heart failure.

SUMMARY OF THE INVENTION

A therapeutic method for treating a human or animal subject afflicted with congestive heart failure is provided comprising the step of administering an effective selective antagonist for arginine vasopressin to the subject. The mode of administration is preferably via application by an atomized spray of the selective antagonist to the nasal mucosae. Alternatively, the antagonist may be administered by intravenous injection.

DETAILED DESCRIPTION OF THE FIGURES

Figure 2:
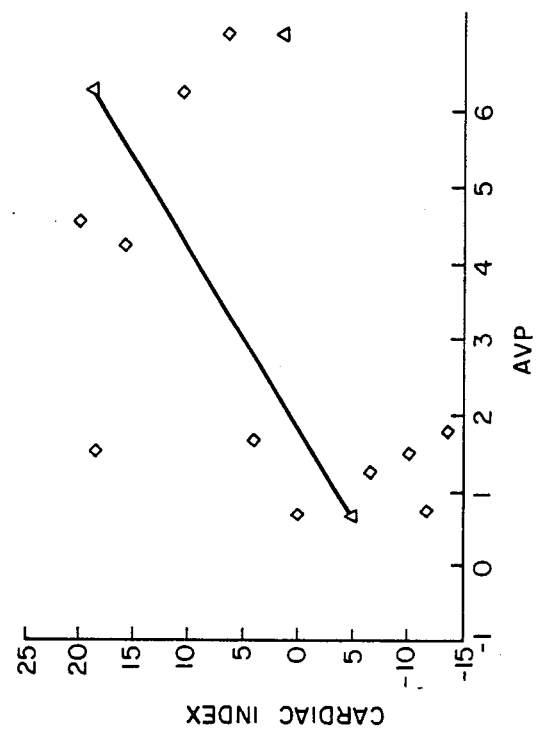
Figure 1:
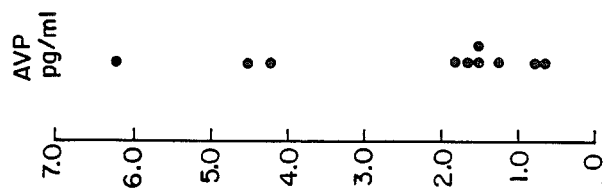

The present invention may be more fully and easily understood when taken in conjunction with the accompanying drawing, in which:

FIG. 1 is a graph illustrating the baseline concentration of plasma arginine vasopressin in each of ten different human patients under test; and FIG. 2 is a graph illustrating the change in systemic vascular resistance following administration of a selective antagonist.

DETAILED DESCRIPTION OF THE PREFERRED EMBODIMENTS

The present invention is a therapeutic method for treating human and/or animal subjects afflicted with the pathological condition known as congestive heart failure. The method utilizes a potent and selective class of antagonists for arginine-vasopressin (hereinafter "AVP") which have been previously prepared and evaluated as effective antagonists of vasopressin. There are ten analogues in the class as a whole each of which conforms to the following general structure:

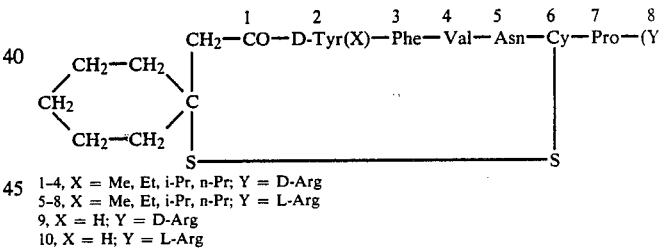

1-4, X = Me, Et, i-Pr, n-Pr; Y = D-Arg
5-8, X = Me, Et, i-Pr, n-Pr; Y = L-Arg
9, X = H; Y = D-Arg
10, X = H; Y = L-Arg

Specifically, the 10 analogues comprising the class are as follows:

1. [1-(β-mercapto-β,β-cyclopentamethylenepropionic acid),2-(O-methyl)-D-tyrosine,4-valine,8-D-arginine]vasopressin;

2. [1-(β-mercapto-β,β-cyclopentamethylenepropionic acid, 2-(O-ethyl)-D-tyrosine,4-valine,8-D-arginine]vasopressin;

3. [1-(β-mercapto-β,β-cyclopentamethylenepropionic acid),2-(O-isopropyl)-D-tyrosine,4-valine,8-D-arginine]vasopressin;

4. [1-(β-mercapto-β,β-cyclopentamethylenepropionic acid),2-(O-n-propyl)-D-tyrosine,4-valine,8-D-arginine]vasopressin;

5. [1-(β-mercapto-β,β-cyclopentamethylenepropionic acid),2-(O-methyl)-D-tyrosine,4-valine]argininevasopressin;

6. [1-(β-mercapto-β,β-cyclopentamethylenepropionic acid),2-(O-ethyl)-D-tyrosine,4-valine]argininevasopressin;

7. [1-(β-mercapto-β,β-cyclopentamethylenepropionic acid),2-(O-isopropyl)-D-tyrosine,4-valine]arginine-vasopressin;

8. [1,(β-mercapto-β,β-cyclopentamethylenepropionic acid),2-(O-n-propyl)-D-Tyrosine,4-valine]arginine-vasopressin;

9. [1-(β-mercapto-β,β-cyclopentamethylenepropionic acid),2-D-tyrosine,4-valine,8-D-arginine]-vasopressin;

10. [1-(β-mercapto-β,β-cyclopentamethylenepropionic acid),2-D-tyrosine,4-valine]arginine-vasopressin.

The analogues are prepared according to the method described by Manning et al. [*J. Med. Chem.* 25: 45–50 (1982)] for modifying previously known weak antagonists by substituting O-alkyl-D-tyrosine at position 2 of 1-(β-mercapto-β,β-cyclopentamethylenepropionic acid),4-valine,8-D-arginine]vasopressin and its L-arginine isomer, [1-(β-mercapto-β,β-cyclopentamethylenepropionic acid),4-valine]arginine-vasopressin. The complete synthesis is described at *J. Med. Chem.* 25: 46 (1982).

In view of the difficulty in preparing these specific antagonist individually, a single representative, [1-(β-mercapto-β,β-cyclopentamethylenepropionic acid),2-(O-methyl)-D-tyrosine,4-valine,8-D-arginine]vasopressin, was custom synthesized by Senn Chemicals (Zurich, Switzerland) and was utilized as the exclusive therapeutic agent in all the empirical tests performed and described herein. It will be explicitly understood, however, that the use of this single antagonist in the detailed description which follows is merely representative and exemplary of the class as a whole; for this reason it is expected that each and every individual analogue in this class will be equally effective as a therapeutic agent for the treatment of congestive heart failure.

For the sake of clarity and commonality of understanding, some definitions of terms frequently used in describing various physiological and pharmacological effects will be provided.

The systemic vascular resistance is the opposition to blood flow in blood vessels which is equal to the pressure drop between the ends of the vessel divided by the flow rate of the blood. The commonly used units of resistance is the "peripheral resistance unit" given as 1 mmHg/sec/ml.

The cardiac index is the cardiac output per square meter of body surface. Under normal conditions, it is equal to 2.5–4.2 liters/minute/square meter.

An agonist of a drug is another drug which competes for the same receptors and has a similar pharmacological effect.

An antagonist is a substance that competes for the same receptors but has no pharmacologic action and therefore nullifies the action of another drug (an agonist) by competitively blocking its receptors.

To demonstrate the therapeutic effectiveness of selective antagonists for vasopressin in subjects afflicted with congestive heart failure, two sets of experimental tests were performed. Each will be described individually.

EXPERIMENTAL SERIES I

Patients

Ten men with chronic congestive heart failure, aged 50–78 years participated in this study. The causes of congestive heart failure were diagnosed as primary cardiomyophathy in seven persons; coronary artery disease in one person; and severe left ventricular dysfunction secondary to valvular heart disease in two persons, both of whom had previously undergone valve replacement. The duration of disease symptoms ranged from two months to five years an averaged 23.5±22 months. Radionuclide measurement of the blood fraction ejected by the left ventricle average 24.1±10.1%.

All evaluations were conducted in the postabsorptive state without premedication. Vasodilator medications were discontinued at least 48 hours prior to the beginning of the experimental series and digitalis and diuretics were withheld for at least 24 hours preceeding each experiment. Clinically indicated antiarrhythmic drugs were continued throughout the protocol. Dietary sodium was restricted to 2.0 grams per day.

Hemodynamic Measurements

A right heart catheterization was performed in each patient of the study utilizing a Swan-Ganz catheter (Edwards Laboratories) and a cannula was placed in the radial artery. Pressures were monitored using a Hewlett-Packard model 1280B strain gauge transducer which was recorded on a direct-writing multigraph (Hewlett-Packard). Mean pressures were monitored by electronic integration. Zero reference was chosen to be at the right atrium estimated to be 5 centimeters vertically beneath the sternal angle of Louis. Heart rate was determined from a simultaneous electrocardiographic signal. Cardiac output was determined in eight patients by thermodilution using an Edwards model 9520A bedside computer averaging three successive measurements differing by less than 10%. In two patients, the cardiac output was determined by the Fick technique using a Beckman Metabolic cart (Beckman Instruments, Inc.) comprising a volume transducer and an oxygen analyzer to determine minute volume oxygen consumption. In those patients, blood was collected for arterial and mixed venous oxygen content and analyzed on an oxygen analyzer (Lexington Instruments Corporation). Measurements were obtained for systolic, diastolic and mean systemic arterial and pulmonary arterial pressure, pulmonary capillary wedge pressure, and right atrial pressure. The left ventricular filling pressure was defined as the pulmonary capillary wedge pressure, or as the pulmonary artery diastolic pressure if this had been found previously to be consistent with the pulmonary capillary wedge pressure. Hemodynamic indices and systemic and pulmonary arteriolar resistances were calculated from pressure and output values according to standard formulas [Yang et al., *Cardiac Catheterization Data To Hemodynamic Parameters*, F. A. Davis, Philadelphia 1978].

Protocol

All the individual persons used in this study were evaluated while lying in the recumbent position. Systemic hemodynamic data were collected until three successive determinations at 15 minute intervals demonstrated homoeostasis. Mixed venous blood was collected for determination of plasma arginine vasopressin concentration. In addition, blood was collected for determination of plasma osmolality, blood urea nitrogen, creatinine, sodium and potassium.

In order to identify the pressor effect of physiological levels of vasopressin, a competitive antagonist of the vasoconstrictor action of arginine vasopressin at the vascular $V_1$ receptors was used. This therapeutic agent, [1-(β-mercapto-β,βcyclopentamethylenepropionic acid),2-(O-methyl),tyrosine]arginine vasopressin, was administered by intravenous injection over a five minute time period at a total dosage of 0.5 milligrams (hereinafter "mg"). This dosage had previously been demonstrated to inhibit 80% of the blood pressure response following administration of exogenous arginine vasopressin at a dose of 20 mU/kg [Gavras et al., *Hypertension* (Suppl. I) 6: 156-160 (1984)]. Hemodynamic measurements were taken at 15, 30, and 60 minutes after administration of the selective antagonist. Blood was collected for chemical analysis 60 minutes following administration of the antagonist.

Hormonal Assays

Plasma vasopressin levels were determined by radioimmunoassay [La Rochelle et al., *Pflugers Archive*. 387: 79-81 (1980)]. Because the antibodies in this assay procedure cross-react with the selective antagonist, the concentration of endogenous arginine vasopressin could not be determined in this manner following administration of the antagonist. Plasma osmolality was measured using the freezing point method.

Results

Of the ten human subjects evaluated in this study, only three were found to have vasopressin levels in excess of normal values. As indicated in FIG. 1. Arginine vasopressin levels ranged from 0.7-6.2 picograms per milliliter (hereinafter "pg/ml") an average 2.4±0.6 pg/ml. As a comparative basis, normal arginine vasopressin values for fully hydrated human subjects were found to be 1.1±0.2 pg/ml with an intraassay and interassay coefficient of variation of less than 6% and less than 10% respectively.

After administration of the vasopressin antagonist, systemic vascular resistance declined and cardiac index increased in each of the three persons whose vasopressin were initially was found to be above normal in concentration. In these three patients, the plasma AVP levels were between 4-6.2 ug/ml as seen in FIG. 2. The maximum effect occurred approximately 30 minutes after administration of the selective antagonist. This is to be contrasted with the absence of meaningful change in the remaining seven patients comprising the test sample.

In evaluating all ten patients as a group, the average results in blood pressure, pulmonary artery pressure, and all other parameters under test are given in Table I below. The changes for the group as a whole are not statistically significant as the results from the three responders are diluted by those of the seven non-responders.

recognized that there is a clinically signficant improvement in thirty percent of persons afflicted with the disease. On the basis of at least this demonstrated thirty percent effectiveness, the value of the administered antagonist as a therapeutic agent is deemed to be demonstrated. The study provides direct evidence that at least some human patients with congestive heart failure whose plasma vasopressin levels exceeded normal values had a systemic vasodilatory response to the administration of the selective antagonist.

EXPERIMENTAL SERIES II

To demonstrate the effectiveness of the vasopressin antagonist when administered as an atomized spray to the nasal mucosae, a study was conducting using normal Wistar rats, each weighing approximately 280-300 grams. On the day before experimental testing, each rat was placed under ether anesthesia, and the right iliac artery and the right external jugular vein were catherized with PE-50 tubing. On the day following surgery, with the animal remaining unrestrained, the mean arterial pressure was monitored via a Hewlett-Packard 1280C transducer and a 7702B Recorder.

Materials and Methods

A vasopressin injection was prepared by diluting commercially obtained Pitressin at 20 U/ml concentration with 5% dextrose in water (hereinafter "D5W") to yield a sterile 20 mU/ml final concentration. A selective antagonist solution was prepared by diluting the pulverized agent, [1-($\beta$-mercapto-$\beta,\beta$-cyclopentamethylenepropionic acid), 2-(O-methyl)tyrosine]arginine vasopressin, in D5W to provide a 2.5 mg/ml solution. All intravenous injections of vasopressin were flushed through using an additional volume comprising 0.2-0.3 ml of D5W.

Each experimental animal was tested in two stages: initially, two 0.1 ml injections each containing 2.0 millipressor units of arginine vasopressin were given through the venous catheter over a ten minute period and the individual changes in mean arterial pressure recorded. This stage identified each of the test animals as being susceptible to the physiological effects of vasopressin. The second stage of the experiment comprised release of 0.1 ml containing 250 ug of the selective antagonist onto the nasal mucosae of the rat via a PE-50 catheter which had been inserted into one of the nostrils to a depth of about four millimeters. This administration of the antagonist as a nasal spray onto the mucosae of

TABLE I

| | Hemodynamic response to the AVP antagonist | | | | | | | | |
|---|---|---|---|---|---|---|---|---|---|
| | BP mmHg | PAP mmHg | LVFP mmHg | RAP mmHg | HR BPM | CI 1/min/2$^2$ | SVI m/m$^2$ | SVR d.s.c.$^{-5}$ | PAR d.s.c.$^{-5}$ |
| Baseline | 85.7 + 2.8 | 36.2 ± 2.1 | 23.9 ± 2.0 | 11.3 ± 2.3 | 88.7 ± 3.8 | 2.0 ± 0.2 | 23.5 ± 2.5 | 1752 ± 259 | 291 ± 43 |
| AVP Antagonist | 88.5 + 3.2 | 37.1 ± 2.2 | 24.5 ± 2.3 | 10.0 ± 2.3 | 89.0 ± 4.4 | 2.1 ± 0.2 | 24.6 ± 2.6 | 1810 ± 312 | 280 ± 44 |

Values are presented as mean ± SEM for all 10 patients. BP denotes mean blood pressure; PAP, mean pulmonary artery pressure; LVFP, left ventricular filling pressure; RAP, right atrial pressure; HR, heart rate, CI cardiac index; SVI, stroke volume index; SVR, systemic vascular resistance; PAR, pulmonary arteriolar resistance.

For the ten patients as a group, therefore, the baseline plasma arginine vasopressin ("AVP") levels correlated inversely with the percent change in systemic vascular resistance (r=−0.70, p=0.025) and approached a significant correlation with the percent change in cardiac index (r=0.62, p=0.06). It should be recognized however that for the group tested as a whole, the antagonist cause no significant change in systolic, diastolic or mean blood pressure, or other pressures as measured in Table I. Furthermore, there were no significant changes in cardiac index or stroke volume index. Nevertheless, it is the nose was followed by repeated injection of 0.1 ml volumes, each containing 2.0 millipressor units of arginine vasopressin, at 10, 20, 30, 60, and 120 minutes after the administration of the selective antagonist. The change in mean arterial pressure was recorded at each of these intervals after each injection of the vasopressin.

Results

The results of these empirical tests are given by Table II below.

TABLE II

| | Changes in Mean Arterial Pressure (mm Hg) | | | | | |
|---|---|---|---|---|---|---|
| | After AVP | After Antagonist Adm. + AVP Injections | | | | |
| Rat # | Injection Alone | 10' | 20' | 30' | 60' | 120' |
| 1 | +37.5 | 0 | 0 | 0 | 0 | 0 |
| 2 | +38.5 | +5 | 0 | +5 | 0 | 0 |
| 3 | +29.0 | 0 | +5 | +5 | +5 | +5 |

It will be noted that initially the administration of 2.0 millipressor units of arginine vasopressin produced a mean change in arterial pressure of about 35 mmHg in the three test animals. Accordingly, each rat under test demonstrated its sensitivity to vasopressin. The second stage of testing demonstrates the efficacy of administering the selective antagonist as an atomized nasal spray to the nasal mucosa and reveals the ability of the selective antagonist to act as a pre-inhibitor thereby avoiding the pharmacological effects of vasopressin. In particular, after a nasal spraying of 250 ug of selective inhibitor, the injection of 2.0 mU of vasopressin repeatedly had no significant effect for at least the two hours comprising the duration of the test. It is thus demonstrated that the selective antagonist may be administered effectively as a nasal spray applied to the mucosae and that the effects of this mode of administration are both long term and substantively effective against vasopressin.

The ten selective antagonists comprising the class as a whole may be used as therapeutic agents individually or in combination as desired or required under the clinical conditions. The concentration and frequency of administration to a human subject will vary with the clinical health and state of the patient and with the mode of administration. Typically, using the nasal spray route of administration to the mucosae, it is preferred that 0.1 ml of fluid volume be atomized into spray form and that this 0.1 ml fluid volume contain 250 ul of at least one of the selective antagonist. It is also desirable that an average therapeutic dose of 500 ug of selective antagonist be applied in each instance of therapeutic use. Similarly, should the intravenous injection mode of administration be desired, an average therapeutic dose of 0.5 mg is deemed to be therapeutically effective. This dosage may be repeated periodically. In each instance, it is expected that an inert fluid will serve to volumetrically carry the selective antagonist into the tissues of the subject. It is expected also that the therapeutic regiment will require repeated dosages of selective antagonist at set intervals of between 4 and 6 hours in order to achieve maximum benefits for the afflicted patients.

The present invention is not to be restricted in form nor limited in scope except by the claims appended hereto.

What I claim is:

1. A therapeutic method for treating a subject afflicted with congestive heart failure comprising the step of administering an effective amount of an antagonist selective for arginine-vasopressin to the subject.

2. The therapeutic method as recited in claim 1 wherein said selective antagonist is [1-(β-mercapto-β,β-cyclopentamethylenepropionic acid), 2-(O-methyl)-tyrosine]arginine vasopressin.

3. The therapeutic method as recited in claim 1 wherein said selective antagonist is selected from the group consisting of:

[1-(β-mercapto-β,βcyclopentamethylenepropionic acid),2-(O-methyl)-D-tyrosine,4-valine,8-D-arginine]vasopressin; [1-(β-mercapto-β,β-cyclopentamethylenepropionic acid,2-(O-ethyl)-D-tyrosine,4-valine,8-D-arginine]vasopressin; [1-(β-mercapto-β,β-cyclopentamethylenepropionic acid),2-(O-isopropyl)-D-tyrosine,4-valine,8-D-arginine]vasopressin; [1-(β-mercapto-β,β-cyclopentamethylenepropionic acid),2-(O-n-propyl)-D-tyrosine,4-valine,8-D-arginine]-vasopressin; [1-(β-mercapto-β,β-cyclopentamethylenepropionic acid),2-(O-methyl)-D-tyrosine,4-valine]arginine-vasopressin; [1-(β-mercapto-β,β-cyclopentamethylenepropionic acid),2-(O-ethyl)-D-tyrosine,4-valine]arginine-vasopressin; [1-(β-mercapto-β,β-cyclopentamethylenepropionic acid),2-(O-isopropyl)-D-tyrosine,4-valine]arginine-vasopressin; [1-(β-mercapto-β,β-cyclopentamethylenepropionic acid),2-(O-n-propyl)-D-Tyrosine,4-valine]arginine-vasopressin; [1,(β-mercapto-β,β-cyclopentamethylenepropionic acid),2-D-tyrosine,4-valine,8-D-arginine]vasopressin; and [1-(β-mercapto-β,β-cyclopentamethylenepropionic acid),2-D-tyrosine,4-valine]arginine-vasopressin.

4. The therapeutic method as recited in claim 1 wherein said administration is via the nasal mucosae.

5. The therapeutic method as recited in claim 1 wherein said administration is by intravenous injection.

* * * * *